United States Patent [19]

Saltzman

[11] 4,029,775
[45] June 14, 1977

[54] ANTIMICROBIAL COMPOSITIONS

[75] Inventor: William H. Saltzman, New Rochelle, N.Y.

[73] Assignee: Intellectual Property Development Corporation, New Rochelle, N.Y.

[22] Filed: Dec. 29, 1975

[21] Appl. No.: 644,688

Related U.S. Application Data

[63] Continuation-in-part of Ser. No. 523,627, Nov. 14, 1974, Pat. No. 3,931,403, which is a continuation of Ser. No. 363,460, May 25, 1973, abandoned.

[52] U.S. Cl. .......................... 424/238; 260/397.1; 260/397.2
[51] Int. Cl.$^2$ .................... C07J 9/00; A61K 31/56
[58] Field of Search ............... 424/238; 260/397.1, 260/397.2

[56] References Cited

UNITED STATES PATENTS

| | | | |
|---|---|---|---|
| 3,833,620 | 9/1974 | Saltzman | 260/397.1 |
| 3,839,565 | 10/1974 | Saltzman | 260/397.2 |

Primary Examiner—Elbert L. Roberts

[57] ABSTRACT

This invention relates to new physiologically active materials and to methods for their use. The novel compositions of this invention are comprised of an active ingredient of the formula:

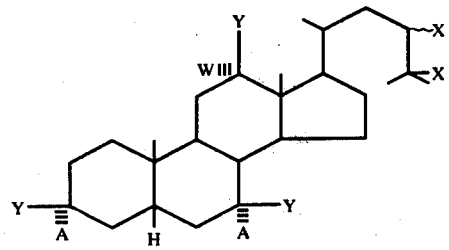

wherein each
  Y is hydrogen;
each
  A is hydroxy, acyloxy or alkoxy;
  W is hydrogen, hydroxy, acyloxy, or alkoxy;
  A and Y when taken together, is oxo (O=);
  W and Y when taken together, is oxo (O=);
each
  X is hydrogen, hydroxy, acyloxy or alkoxy, at least one X being hydroxy;

and the non-toxic, pharmaceutically acceptable salts thereof.

8 Claims, No Drawings

ANTIMICROBIAL COMPOSITIONS

This application is a continuation in part of my previously filed copending application Ser. No. 523,627, filed Nov. 14, 1974 now U.S. Pat. No. 3,931,403, which in turn is a continuation application of previously filed application Ser. No. 363,460, filed May 25, 1973 now abandoned.

This invention relates to novel, physiologically active compositions which possess antimicrobial, antibiotic and bacteriostatic properties. More particularly, this invention relates to antimicrobial, antibiotic and bacteriostatic compositions having as their active ingredient a compound of the formula:

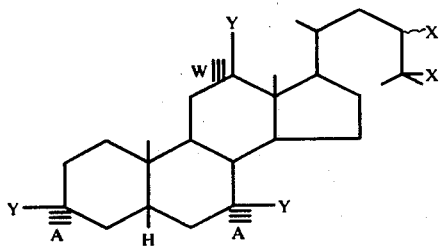

wherein each
Y is hydrogen;
each
  A is hydroxy, acyloxy or alkoxy;
  W is hydrogen, hydroxy, acyloxy, or alkoxy;
  A and Y when taken together is oxo (O=);
  W and Y when taken together is oxo (O=);
each
  X is hydrogen, hydroxy, acyloxy, or alkoxy, at least one X being hydroxy;
and the non-toxic pharmaceutically acceptable salts thereof.

The compositions of this invention possess antimicrobial, antibiotic and/or bacteriostatic properties and may be useful in the control of various microorganisms, especially certain anaerobic organisms. In addition, the compositions of this invention also appear to possess microorganism enzyme inactivation properties.

The preferred alkoxy radicals of the compounds of this invention are those which are comprised of six or less carbon atoms, and include such moieties as methyl, ethyl, propyl, butyl, pentyl, and hexyl.

The acyloxy radicals of the compounds of this invention are those from hydrocarbon carboxylic acids of less than twelve carbon atoms, and include such acids as the alkanoic acids, the alkenoic acids, the monocyclic aralkyl carboxylic acids, the monocyclis aryl carboxylic acids, the cycloalkane carboxylic acids, and the cycloalkene carboxylic acids.

Whenever in this application and the claims appended thereto, in any chemical structure set forth therein, a curved line ( $\{$ ) is employed in the linkage of atoms, it is meant to denote that the connected atom or moiety may be in the alpha- or beta- position as the case may be.

The compositions of this invention possess antimicrobial, antibiotic and/or bacteriostatic and/or bacterial enzyme inactivating activity and for this purpose may be administered to the patient suffering from such conditions as intestinal bacterial infections. The amount and the route of administration of the compositions of this invention can be adjusted by the skilled worker in accordance with the conditions of the patient being treated and his requirements and the potency of the composition being employed. The compositions of this invention may be administered to the patient in any manner which may be deemed acceptable to the skilled worker practicing the invention. Most preferably, the compositions of this invention may be administered perorally to the patient being treated. For this purpose, the compositions of this invention may be prepared in such suitable pharmaceutically acceptable final dosage forms as may be employed by the skilled worker. Thus, commonly employed pharmaceutically acceptable dosage forms suitable for oral administration containing the active compounds of this invention in sufficient concentration to attain the desired results may be utilized. Pharmaceutically acceptable non-toxic inert carriers which are usually employed for such purposes may be utilized to prepare such dosage forms as tablets, capsules, elixirs, solutions, suspensions and the like. Satisfactory results in the practice of this invention may be obtained by the administration of small but effective amounts of the compositions and compounds of this invention to the patient being treated. Satisfactory results may be obtained when from 10 to 1500 mg. of the active compounds of this invention are daily administered to the patient being treated hereunder. In the use of tablet or capsule final dosage forms of the compositions of this invention, may be present from 10 to 500 mg of the compounds of this invention, although other concentrations may also provide satisfactory results.

The compounds of this invention may be prepared in accordance with the process of this invention commencing with cholic acid and its derivatives as starting materials. The process of preparing the final compounds of this invention may be illustrated by the following equations:

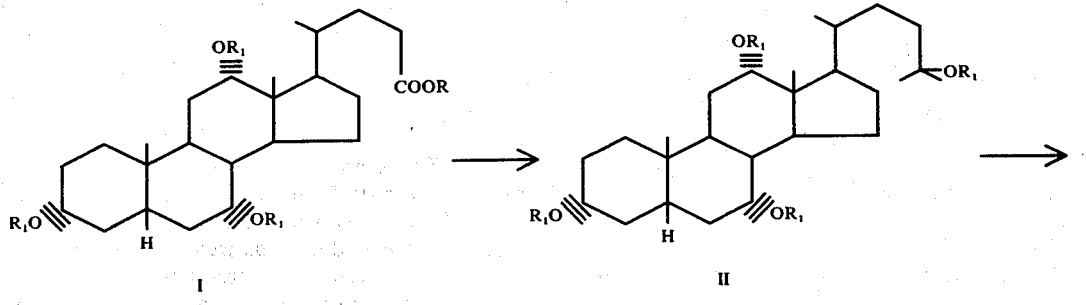

A₁R = R₁ = H
BR₁ = H; R = CH₃

A₁R₁ = H

-continued

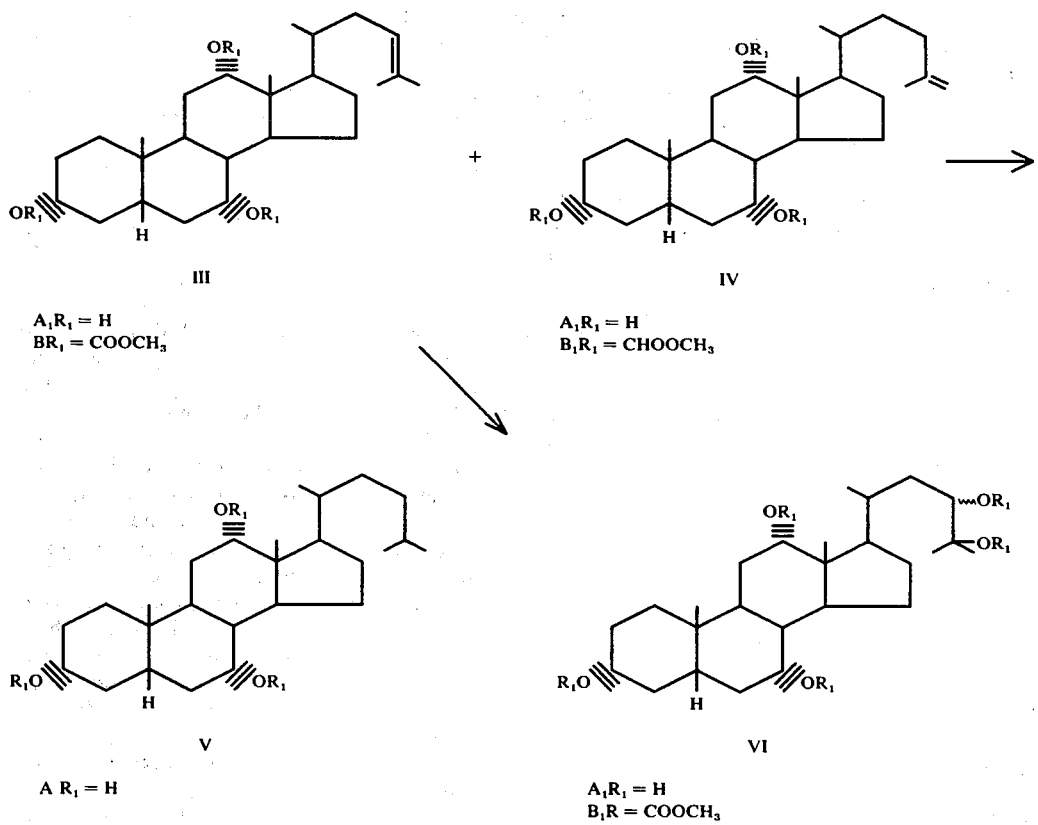

III
A,R₁ = H
BR₁ = COOCH₃

IV
A,R₁ = H
B,R₁ = CHOOCH₃

V
A R₁ = H

VI
A,R₁ = H
B,R = COOCH₃

In general, the process of this invention entails a number of steps beginning with cholic acid or its derivatives, e.g. methyl cholate as starting materials. In the first step of the process of this invention, the cholic acid starting material, for example, methyl cholate (Compound IB) is subjected to a Grignard reaction to yield the 3,7,12,24 tetrol derivative, Compound IIA. Compound IIA was then acidified, by treatment with an organic acid, for example, acetic or glacial acetic acid, or a combination of both, to yield a combination of the corresponding 23 or 24-ene triacyloxy derivatives, Compounds IIIB, and IVB. Compounds IIIB and IVB may then be hydrodyzed to yield the corresponding 23 or 24-ene-triols (Compounds IIIA and IVA), by treatment with an alkali metal base, for example KOH in an alcohol medium, for example, methanol. Compounds III and IV may then be further treated for example, by hydrogenation by treatment with hydrogen in the presence of a platinum on carbon catalyst to yield the 26 carbon triols of Compounds V. The 23-ene triol of Compound III may then be oxidized, by treatment with an oxidizing agent, for example osmium tetroxide to yield the desired pentol products of the instant invention (Compounds VI).

The invention may be further illustrated by the following examples.

EXAMPLE 1

24-Methyl-25-homo-5-cholane-3α, 7α, 12α, 24-tetrol

Methyl cholate (5.7 g) dissolved in dry benzene (160 ml) was added to 90 ml of 2M methyl magnesium iodide dissolved in dry ethyl ether. The crude tetrol 4.8 g (85%) was recrystallized from ethyl acetate/methanol, and from methanol. The crystals had a m.p. of 119°-121° C.

EXAMPLE 2

24-Methyl-25-homo-5 -chol-23-ene-3α, 7α, 12α-triol and 24-methyl-25-homo-24-ene-3α, 7α, 12α-triol The tetrol of Example 1 (3.06 g), 100 ml of glacial acetic acid, and 70 ml of acetic anhydride were refluxed for 24 hr. The cooled solution was concentrated in vacuo and the residue was treated with 200 ml of ice-cold water and the white ppt. was collected.

Two grams of the triacetoxy mixture were hydrolyzed in a 60° C. water bath with 100 ml of 6% methanolic KOH for 3 hours. The hydrolyzate was poured into a beaker with crushed ice, stirred and the white precipitate was collected. A mixture of 23-ene and 24-ene triol (IIIA and IVA) (230 mg) was separated on a 40 cm × 2 cm column, containing 40 of 25% AgNO₃ silicic acid. The products were eluted with increasing amounts of ethyl acetate in benzene. Pure 23-ene-triol was eluted with 70% ethyl acetate in banzene and 24-ene triol gave a m.p. of 190°-191° C. The 24-ene triol had a melting point of 166°-169° C.

EXAMPLE 3

One gram of the tetrol of Example 1 was refluxed for 20 hr with 50 ml acetic acid and 5 ml of acetic anhydride. The cooled solution was concentrated in vacuo and the residue was treated with ice-cold water. The oily product was extracted with benzene and evaporated, and the residue was the 23-ene-triacetate (Compound IIIB).

EXAMPLE 4

A mixture of unsaturated sterols (200 mg) was obtained as described in Example 2 above, dissolved in 30 ml of ethyl acetate was hydrogenated for 12 hrs. at 25° C. with a platinum on carbon catalyst (35 mg). The catalyst was filtered off and the solvent was evaporated. Crystallization of the resulting compound from ethyl acetate gave white crystalline material (Compound V) (130 mg), m.p. 182°–184° C.

EXAMPLE 5

The 23-ene triacetate (400 mg) of Example 3, was carefully dried and dissolved in 30 ml of anhydrous ethyl ether and 2 ml of anhydrous pyridine. Osmium tetroxide (0.5 g) dissolved in 6 ml of anhydrous ethyl ether was added, the solution was stoppered and left for 60 hrs. The crude pentol (272 mg) was purified by column chromatography on neutral alumina V with increasing amounts of methanol in ethyl acetate (10). The fractions were monitored by TLC on silica gel G plates of 0.25 mm thickness (Brinkmann) solvent system chloroform: acetone: methanol (70:50:15, v/v/v). The fractions eluted with 7–12% methanol in ethyl acetate contained 207 mg of the 3α, 7α, 12α, 23, 24-pentol (Compound VI). Crystallization from ethyl acetate gave a white crystalline material, m.p. 172°–175° C.

The invention may be variously otherwise embodied within the scope of the appended claims.

What is claimed is:

1. A composition possessing antimicrobial, antibiotic or bacteriostatic properties comprising a combination of from 10 to 500 milligrams of a compound of the formula

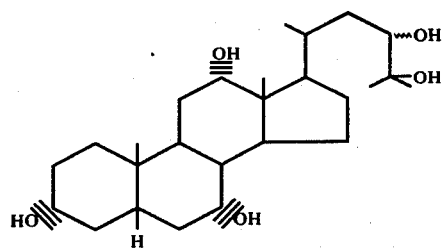

wherein
  Y is hydrogen, hydroxy or acyloxy;
wherein each
  X is hydroxy or acyloxy; and a pharmaceutically acceptable non-toxic carrier.

2. The composition of claim 1 wherein each X is hydroxy.

3. The composition of claim 1 wherein the compound has the formula

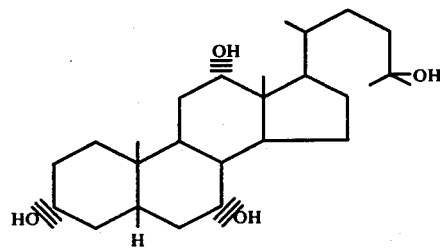

4. The composition of claim 1 wherein the compound has the formula

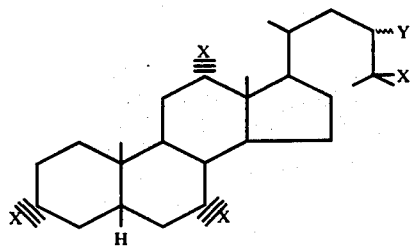

5. A compound of the formula wherein
  Y is hydrogen, hydroxy or acyloxy;
and each
  X is hydroxy or acyloxy.

6. The compound of claim 5 wherein each X is hydroxy

7. The compound of claim 5 wherein each X is hydroxy, and Y is hydroxy.

8. The compound of claim 5 wherein each X is hydroxy and Y is β-hydroxy.

* * * * *